US011919283B2

(12) United States Patent
Hjelmgaard et al.

(10) Patent No.: US 11,919,283 B2
(45) Date of Patent: *Mar. 5, 2024

(54) METHOD OF PROVIDING INSULATION TO A STRUCTURE

(71) Applicant: ROCKWOOL INTERNATIONAL A/S, Hedehusene (DK)

(72) Inventors: Thomas Hjelmgaard, Fredensborg (DK); Lars Hald, Hedehusene (DK); Thomas Tielemann, Vreden (DE)

(73) Assignee: ROCKWOOL A/S, Hedehusense (DK)

( * ) Notice: Subject to any disclaimer, the term of this patent is extended or adjusted under 35 U.S.C. 154(b) by 1514 days.

This patent is subject to a terminal disclaimer.

(21) Appl. No.: 16/300,608

(22) PCT Filed: May 11, 2017

(86) PCT No.: PCT/EP2017/061413
§ 371 (c)(1),
(2) Date: Nov. 12, 2018

(87) PCT Pub. No.: WO2017/194719
PCT Pub. Date: Nov. 16, 2017

(65) Prior Publication Data
US 2020/0308355 A1 Oct. 1, 2020

(30) Foreign Application Priority Data

May 13, 2016 (EP) .................................. 16169635
May 13, 2016 (EP) .................................. 16169638
May 13, 2016 (EP) .................................. 16169641

(51) Int. Cl.
B32B 37/12 (2006.01)
B32B 5/12 (2006.01)
(Continued)

(52) U.S. Cl.
CPC ............... *B32B 37/12* (2013.01); *B32B 5/12* (2013.01); *B32B 5/26* (2013.01); *B32B 7/12* (2013.01); *B32B 15/14* (2013.01); *B32B 19/04* (2013.01); *B32B 19/041* (2013.01); *B32B 37/1207* (2013.01); *B32B 37/146* (2013.01); *B32B 37/18* (2013.01); *B32B 38/0004* (2013.01); *C03C 13/06* (2013.01); *C03C 25/26* (2013.01); *C03C 25/32* (2013.01); *C03C 25/321* (2013.01); *C03C 25/328* (2013.01); *C08J 5/043* (2013.01); *C08L 1/286* (2013.01); *C08L 3/02* (2013.01); *C08L 5/12* (2013.01); *C08L 89/06* (2013.01); *C09H 11/00* (2013.01); *C09J 5/00* (2013.01); *C09J 11/06* (2013.01); *C09J 101/28* (2013.01); *C09J 101/286* (2013.01); *C09J 103/02* (2013.01); *C09J 105/00* (2013.01); *C09J 105/04* (2013.01); *C09J 105/06* (2013.01); *C09J 105/12* (2013.01); *C09J 189/005* (2013.01); *C09J 189/06* (2013.01); *D04H 1/413* (2013.01); *D04H 1/4209* (2013.01); *D04H 1/4218* (2013.01); *D04H 1/4266* (2013.01); *D04H 1/587* (2013.01); *D04H 1/593* (2013.01); *D04H 1/64* (2013.01); *D04H 1/724* (2013.01); *D04H 1/74* (2013.01); *D04H 3/002* (2013.01); *D04H 3/004* (2013.01); *E04B 1/74* (2013.01); *E04B 1/80* (2013.01); *E04B 1/88* (2013.01); *E04B 1/94* (2013.01); *E04C 2/284* (2013.01); *E04D 3/352* (2013.01); *E04F 13/0866* (2013.01); *B32B 2037/1215* (2013.01); *B32B 2037/1253* (2013.01); *B32B 2037/1269* (2013.01); *B32B 38/164* (2013.01); *B32B 2250/20* (2013.01); *B32B 2250/40* (2013.01); *B32B 2255/02* (2013.01); *B32B 2255/26* (2013.01);
(Continued)

(58) Field of Classification Search
CPC ..... E04B 1/74; E04B 1/88; E04B 1/94; E04C 2/284; C03C 13/06; C03C 13/26; C03C 13/32; C03C 13/321
See application file for complete search history.

(56) References Cited

U.S. PATENT DOCUMENTS 4,773,960 A * 9/1988 Vincelli ................ B05B 7/1409
406/48
4,822,679 A * 4/1989 Cerdan-Diaz ........... C04B 30/02
428/389
11,174,578 B2 * 11/2021 Hjelmgaard ............ B32B 19/04

FOREIGN PATENT DOCUMENTS

CN 102459320 A 5/2012
CN 103476300 A 12/2013
(Continued)

OTHER PUBLICATIONS

CN Office Action dated Dec. 26, 2019 for corresponding CN Application No. 201780028793.X.
(Continued)

Primary Examiner — C Melissa Koslow
(74) Attorney, Agent, or Firm — TAROLLI, SUNDHEIM, COVELL & TUMMINO L.L.P.

(57) ABSTRACT

The present invention relates to a method of providing thermal and/or acoustic insulation to a structure, comprising the steps of: providing a substrate which comprises fibres; applying the substrate to the structure; blending the substrate with a binder composition before, during or after application of the substrate to the structure; allowing curing of the binder composition after the substrate and the binder composition have been applied to the structure; wherein the binder composition comprises at least one hydrocolloid. The present invention also relates to an insulated structure obtainable by said method.

34 Claims, No Drawings

(51) Int. Cl.
| | |
|---|---|
| B32B 5/26 | (2006.01) |
| B32B 7/12 | (2006.01) |
| B32B 15/14 | (2006.01) |
| B32B 19/04 | (2006.01) |
| B32B 37/14 | (2006.01) |
| B32B 37/18 | (2006.01) |
| B32B 38/00 | (2006.01) |
| C03C 13/06 | (2006.01) |
| C03C 25/26 | (2018.01) |
| C03C 25/32 | (2018.01) |
| C03C 25/321 | (2018.01) |
| C03C 25/328 | (2018.01) |
| C08J 5/04 | (2006.01) |
| C08L 1/28 | (2006.01) |
| C08L 3/02 | (2006.01) |
| C08L 5/12 | (2006.01) |
| C08L 89/06 | (2006.01) |
| C09J 5/00 | (2006.01) |
| C09J 11/06 | (2006.01) |
| C09J 101/28 | (2006.01) |
| C09J 103/02 | (2006.01) |
| C09J 105/00 | (2006.01) |
| C09J 105/04 | (2006.01) |
| C09J 105/06 | (2006.01) |
| C09J 105/12 | (2006.01) |
| C09J 189/00 | (2006.01) |
| C09J 189/06 | (2006.01) |
| D04H 1/413 | (2012.01) |
| D04H 1/4209 | (2012.01) |
| D04H 1/4218 | (2012.01) |
| D04H 1/4266 | (2012.01) |
| D04H 1/587 | (2012.01) |
| D04H 1/593 | (2012.01) |
| D04H 1/64 | (2012.01) |
| D04H 1/724 | (2012.01) |
| D04H 1/74 | (2006.01) |
| D04H 3/002 | (2012.01) |
| D04H 3/004 | (2012.01) |
| E04B 1/74 | (2006.01) |
| E04B 1/80 | (2006.01) |
| E04B 1/88 | (2006.01) |
| E04B 1/94 | (2006.01) |
| E04C 2/284 | (2006.01) |
| E04D 3/35 | (2006.01) |
| E04F 13/08 | (2006.01) |
| C12N 9/02 | (2006.01) |
| C12N 9/06 | (2006.01) |
| C12N 9/08 | (2006.01) |
| C12N 9/10 | (2006.01) |
| C12N 9/90 | (2006.01) |
| E04B 1/76 | (2006.01) |

(52) U.S. Cl.
CPC ..... B32B 2262/108 (2013.01); B32B 2305/20 (2013.01); B32B 2305/72 (2013.01); B32B 2307/304 (2013.01); B32B 2307/732 (2013.01); B32B 2309/02 (2013.01); B32B 2315/14 (2013.01); B32B 2317/00 (2013.01); B32B 2419/06 (2013.01); B32B 2607/00 (2013.01); C03C 2213/00 (2013.01); C03C 2218/11 (2013.01); C08J 2301/28 (2013.01); C08J 2303/02 (2013.01); C08J 2389/06 (2013.01); C08J 2405/00 (2013.01); C08J 2405/04 (2013.01); C08J 2405/06 (2013.01); C08J 2405/12 (2013.01); C08J 2491/00 (2013.01); C08J 2493/00 (2013.01); C08L 2201/52 (2013.01); C08L 2205/03 (2013.01); C09J 2400/146 (2013.01); C09J 2401/00 (2013.01); C09J 2403/00 (2013.01); C09J 2405/00 (2013.01); C09J 2489/00 (2013.01); C12N 9/0022 (2013.01); C12N 9/0051 (2013.01); C12N 9/0059 (2013.01); C12N 9/0065 (2013.01); C12N 9/0071 (2013.01); C12N 9/1044 (2013.01); C12N 9/90 (2013.01); C12Y 104/03013 (2013.01); C12Y 108/03002 (2013.01); C12Y 110/03001 (2013.01); C12Y 111/01007 (2013.01); C12Y 114/18001 (2013.01); C12Y 203/01013 (2013.01); C12Y 203/02013 (2013.01); C12Y 503/04001 (2013.01); D10B 2505/20 (2013.01); E04B 2001/742 (2013.01); E04B 2001/743 (2013.01); E04B 2001/745 (2013.01); E04B 2001/7683 (2013.01)

(56) References Cited

FOREIGN PATENT DOCUMENTS

| | | |
|---|---|---|
| CN | 105143141 A | 12/2019 |
| EP | 2738232 A1 | 6/2014 |
| EP | 2990494 A1 | 3/2016 |
| WO | 99/36368 A1 | 7/1999 |
| WO | 01/05725 A1 | 1/2001 |
| WO | 01/96460 A2 | 12/2001 |
| WO | 02/06178 A1 | 1/2002 |
| WO | 2004/007615 A1 | 1/2004 |
| WO | 2006/061249 A1 | 6/2006 |
| WO | 2007/014236 A1 | 2/2007 |
| WO | 2008/023032 A1 | 2/2008 |
| WO | 2009/080938 A2 | 7/2009 |
| WO | 2010/125163 A1 | 11/2010 |
| WO | 2010129200 A1 | 11/2010 |
| WO | 2011/138458 A1 | 11/2011 |
| WO | 2012/118939 A1 | 9/2012 |
| WO | WO 2012/118939 * | 9/2012 |
| WO | 2016/102444 A1 | 6/2016 |

OTHER PUBLICATIONS

Hiller, Shari "Starching fabrics to walls creates fantastic looks", Dec. 29, 2009, http://mattandshari.com/decorating/decorating-ideas/starching-fabric-to-walls-creates-fantastic-looks.

PCT International Search Report for corresponding PCT Application Serial No. PCT/EP2017/061413, dated Jul. 31, 2017, pp. 1-6.

* cited by examiner

METHOD OF PROVIDING INSULATION TO A STRUCTURE

RELATED APPLICATIONS

The present application is a U.S. National Stage Application under 35 USC 371, claiming priority to PCT Serial No. PCT/EP2017/061413, filed on May 11, 2017; which claims priority to European Patent Application Serial No. 16169635.6, filed on May 13, 2016, European Patent Application Serial No. 16169638.0, filed on May 13, 2016, and European Patent Application Serial No. 16169641.4, filed on May 13, 2016, all of which are incorporated herein by reference.

FIELD OF THE INVENTION

The present invention relates to a method of providing thermal and/or acoustic insulation to a structure by applying a substrate comprising fibres to the structure, and blending the substrate with a binder composition before, during or after application of the substrate to the structure. The present invention also relates to an insulated structure obtainable by this method.

BACKGROUND OF THE INVENTION

Providing insulating material to a structure (e.g. a building, a building component, such as e.g. a structural beam or a part of a building) is an important consideration in many construction projects. Materials which provide thermal insulation can significantly reduce the energy requirements of a building, whilst materials which provide acoustic insulation can reduce or eliminate unwanted, exterior noise. Some insulating materials also improve the fire resistance of building structures. Insulating material typically comprises particulate material and/or fibres, which provide the insulating effect.

Insulating material comprising fibres comes in many different forms. For example, rigid forms such as panels, batts and blankets can be cut and placed in the structure to be insulated. Alternatively, it may be in loose-fill or spray-foam form.

In order to form such insulating products, the fibres—optionally in combination with particulate material—are normally bonded together. Typically, a binder composition is mixed with the fibres and/or particulate material and then formed into the insulating product e.g. panels, batts, blankets or loose-fill material that are subsequently applied to the structure.

Insulating products are often required in parts of a building which are difficult to reach, or have unconventional shapes. It is therefore desirable to produce insulating material which can be conveniently sprayed or blown into the desired parts of the structure on-site. An often used insulating material is mineral wool granulate that is provided with a binder. Typically, any binder composition that is present in the insulating material to be sprayed onto the structure forms part of the particulate material and/or fibres. For example, binder compositions are added to mineral fibres at an early processing stage, since they normally set or cure at elevated temperatures. It is also known to add waterglass during the application of granulate.

In the past, phenol-formaldehyde resins, which can be economically produced, have been used as binder compositions for producing insulating material. However, these binders suffer from the disadvantage that they contain formaldehyde and they are therefore potentially harmful to handle and require protective measures when handling them on-site. Non-phenol-formaldehyde binders which can be used as adhesives are sugar based binders, such as for example the compositions disclosed in EP2990494A1, PCT/EP2015/080758, WO2007/014236, WO2011/138458 and WO2009/080938.

Another group of non-phenol-formaldehyde binders are the addition/-elimination reaction products of aliphatic and/or aromatic anhydrides with alkanolamines, e.g., as disclosed in WO 99/36368, WO 01/05725, WO 01/96460, WO 02/06178, WO 2004/007615 and WO 2006/061249. These binder compositions are water soluble and exhibit excellent binding properties in terms of curing speed and curing density. WO 2008/023032 discloses urea-modified binders of that type which provide mineral wool products having reduced moisture take-up.

Since some of the starting materials used in the production of these binders are rather expensive chemicals, there is an on-going need to provide formaldehyde-free binders which are economically produced.

A further effect in connection with previously known aqueous binder compositions for insulating material is that at least the majority of the starting materials used for the productions of these binders stem from fossil fuels. There is an on-going trend of consumers to prefer products that are fully or at least partly produced from renewable materials and there is therefore a need to provide binders for insulating material which are at least partly produced from renewable materials.

A further effect in connection with previously known aqueous binder compositions for insulating material is that they involve components which are corrosive and/or harmful. This requires protective measures for the machinery involved in the production of insulating products to prevent corrosion and also requires safety measures for the persons handling this machinery. This leads to increased costs and health issues and there is therefore a need to provide binder compositions for insulating products with a reduced content of corrosive and/or harmful materials.

A yet further effect in connection with previously known aqueous binder compositions for insulating material is that these binders are conventionally associated with extensive curing equipment for curing the binder. The curing equipment is conventionally an oven operating at temperatures far above 100° C. such as around 200° C., which is associated with extensive energy consumption.

Furthermore, the extensive curing time and high curing temperature required by existing binder compositions means that traditional binder compositions have to be mixed with the fibres at the manufacturing stage i.e. in a factory. It is not possible to mix the binder composition with the binder-free fibres on-site i.e. at the construction stage. This is because it would be impractical and expensive to create the required curing conditions on-site.

In addition to curing conditions that are impractical for on-site application, existing binder compositions, such as those discussed above, often produce harmful substances during the curing process. Therefore, any on-site curing would require protective measures and specific training for the persons carrying out the curing.

SUMMARY OF THE INVENTION

Accordingly, it was an object of the present invention to provide a method of providing thermal and/or acoustic insulation to a structure using a binder composition which has renewable materials as starting materials, and reduces or eliminates corrosive and/or harmful materials.

Further, it was an object of the present invention to provide a method of providing thermal and/or acoustic insulation to a structure using a binder composition which does not require high temperatures for curing.

In addition, it was an object of the present invention to provide a method of providing thermal and/or acoustic insulation to a structure using a binder composition which can be applied to the structure on-site, for example, immediately before, during or after application of the insulating substrate to the structure, and cured on-site.

It was also an object of the present invention to provide a method of providing thermal and/or acoustic insulation to a structure using a binder composition whereby during handling, application, and curing of the binder composition, exposure to harmful substances is minimized and no protective measures are necessary.

In accordance with a first aspect of the present invention, there is provided a method of providing thermal and/or acoustic insulation to a structure, comprising the steps of:
  providing a substrate which comprises fibres;
  applying the substrate to the structure;
  blending the substrate with a binder composition before, during or after application of the substrate to the structure;
  allowing curing of the binder composition after the substrate and the binder composition have been applied to the structure;
wherein the binder composition comprises at least one hydrocolloid.

In accordance with a second aspect of the present invention, there is provided an insulated structure obtainable by the method according to the first aspect of the invention.

The present inventors have surprisingly found that it is possible to provide a method of providing thermal and/or acoustic insulation to a structure, as described above, wherein the binder composition can be produced from renewable materials to a large degree and does not contain, or contains only to a minor degree, any corrosive and/or harmful agents.

In addition, the present inventors surprisingly discovered that since the binder composition used for present method does usually not contain any harmful substances and does usually not set free any harmful substances during the curing, the method can be carried out by any person on-site of use without any protective measures and without a need for specific training for the persons to carry out the method.

Furthermore, the present inventors surprisingly discovered that the binder composition used in the present invention does not require extensive curing times or high curing temperatures; as a result, the insulating material can be applied to the structure on-site and the binder can be allowed to cure on-site.

DESCRIPTION OF THE PREFERRED EMBODIMENTS

In a first aspect of the invention the method of providing thermal and/or acoustic insulation to a structure comprises the steps of:
  providing a substrate which comprises fibres;
  applying the substrate to the structure;
  blending the substrate with a binder composition before, during or after application of the substrate to the structure;
  allowing curing of the binder composition after the substrate and the binder composition have been applied to the structure;
wherein the binder composition comprises at least one hydrocolloid.

The thermal and/or acoustic insulation can be applied to any structure. Usually it is a part of a building. In a preferred embodiment, the structure to be insulated is a wall, a cavity wall, a ceiling, a floor, an attic, or a roof of a building or a building component.

The substrate comprises fibres and preferably also a particulate material. If the particulate material is aerogel it may be present in amounts as high as 45-70 wt %. A fire retarding particulate material may be added, up to a similar wt % amount.

Most preferably the substrate comprising fibres and optionally particulate material does not comprise an initial binder composition before the substrate is blended with the binder composition of the present invention. Thus in such a case the only binder in the final insulated structure is the binder required according to the invention In an embodiment, the substrate does not comprise mineral wool.

Mineral wool substrates generally comprise man-made vitreous fibres (MMVF) such as, e.g., glass fibres, ceramic fibres, basalt fibres, slag wool, mineral wool and stone wool, which are bonded together by a cured mineral wool binder such as a thermoset polymeric binder material.

Natural fibres, synthetic fibres, or a combination of natural and synthetic fibres may be used in the invention.

Suitable natural fibres may be selected from animal fibres, such as sheep's wool, and plant fibres, such as wood wool, cellulosic fibres, cotton fibres, straw, hemp, flax. The natural fibres preferably do not include asbestos.

Suitable synthetic fibres may be inorganic, organic, or a mixture of organic and inorganic fibres.

Suitable synthetic fibres may be selected from aramid fibres, polyacrylonitrile (PAN) fibres, carbon fibres, polyester fibres and polyamide fibres.

Preferably the fibres are inorganic. Most preferably they are mineral fibres such as glass fibres, ceramic fibres or basalt fibres, slag fibres, and stone fibres.

In an embodiment, the mineral fibres are preferably in the form of granulate flocks of fibres bonded with a binder composition.

In this embodiment, the flocks are a granulate product. A granulate product is conventionally made by producing a cured mineral wool web and then subjecting the web to a granulation process so that granules are formed. The granules typically have a size of 1-5 cm and the binder content amounts to an LOI-value typically around 1%. The granules are packaged in a compressed state and the package is then opened at the building site to apply the granulate product with a blowing equipment to e.g. a horizontal attic, in between walls or another structure.

The binder composition is supplied before or during the application of the granulate product, thereby adhering the granules being mineral wool elements to each other. The granules and the binder composition provides a granulate mineral wool product which has improved properties such as being prone to less dusting and providing a more rigid structure which is less prone to collapsing under its own weight.

In an alternative embodiment the granules and the binder composition provides a granulate mineral wool product which adheres to a building structure such as a wall or a ceiling so that the mineral wool product fully or partly coats the building structure.

However, it is preferred that the fibres are in the form of unbonded fibres so that the only binder in the final insulated structure is the binder required according to the invention.

Suitable particulate materials may be one or more selected from aerogel, cellulosic material, perlite, zeolite xonolite, vermiculite and mono-spheres. In a preferred embodiment, the particulate material is aerogel, perlite, vermiculite, phase-change material or fire retardant.

Some fibres and particulates, especially natural materials and synthetic organic fibres, can be sensitive to heat, for example some of these materials have a relatively low melting temperature compared to inorganic fibres. The coherent composite of the invention has the benefit compared to conventional coherent composites that it is still possible to utilize heat-sensitive components, because the binder does not require heat for curing.

In the method of providing insulation according to the present invention, the binder composition comprises at least one hydrocolloid. Usually the binder composition is an aqueous composition.

In a preferred embodiment, the binder compositions are formaldehyde free.

For the purpose of the present application, the term "formaldehyde free" is defined to characterize an insulated product comprising fibres where the emission is below 5 $\mu g/m^2/h$ of formaldehyde from the mass of substrate bonded by the binder, preferably below 3 $\mu g/m^2/h$. Preferably, the test is carried out in accordance with ISO 16000 for testing aldehyde emissions.

A surprising advantage of embodiments of substrates bonded by the binder according to the present invention is that they show self-healing properties. After being exposed to very harsh conditions when a mass of substrate bonded by the binder loses a part of its strength, the bonded substrates according to the present invention can regain a part of, the whole of or even exceed the original strength. In one embodiment, the aged strength is at least 80%, such as at least 90%, such as at least 100%, such as at least 130%, such as at least 150% of the unaged strength. This is in contrast to conventional mineral wool products for which the loss of strength after being exposed to harsh environmental conditions is irreversible.

While not wanting to be bound to any particular theory, the present inventors believe that this surprising property in insulated products comprising fibres according to the present invention is due to the complex nature of the bonds formed in the network of the cured binder composition, such as the protein crosslinked by the phenol and/or quinone containing compound or crosslinked by an enzyme, which also includes quaternary structures and hydrogen bonds and allows bonds in the network to be established after returning to normal environmental conditions. For an insulation product, which when e.g. used as a roof insulation can be exposed to very high temperatures in the summer, this is an important advantage for the long term stability of the product.

Hydrocolloid

Hydrocolloids are hydrophilic polymers, of vegetable, animal, microbial or synthetic origin, that generally contain many hydroxyl groups and may be polyelectrolytes. They are widely used to control the functional properties of aqueous foodstuffs.

Hydrocolloids may be proteins or polysaccharides and are fully or partially soluble in water and are used principally to increase the viscosity of the continuous phase (aqueous phase) i.e. as gelling agent or thickener. They can also be used as emulsifiers since their stabilizing effect on emulsions derives from an increase in viscosity of the aqueous phase.

A hydrocolloid usually consists of mixtures of similar, but not identical molecules and arising from different sources and methods of preparation. The thermal processing and for example, salt content, pH and temperature all affect the physical properties they exhibit. Descriptions of hydrocolloids often present idealized structures but since they are natural products (or derivatives) with structures determined by for example stochastic enzymatic action, not laid down exactly by the genetic code, the structure may vary from the idealized structure.

Many hydrocolloids are polyelectrolytes (for example alginate, gelatine, carboxymethylcellulose and xanthan gum).

Polyelectrolytes are polymers where a significant number of the repeating units bear an electrolyte group. Polycations and polyanions are polyelectrolytes. These groups dissociate in aqueous solutions (water), making the polymers charged. Polyelectrolyte properties are thus similar to both electrolytes (salts) and polymers (high molecular weight compounds) and are sometimes called polysalts.

The charged groups ensure strong hydration, particularly on a per-molecule basis. The presence of counterions and co-ions (ions with the same charge as the polyelectrolyte) introduce complex behavior that is ion-specific.

A proportion of the counterions remain tightly associated with the polyelectrolyte, being trapped in its electrostatic field and so reducing their activity and mobility.

In one embodiment the binder composition comprises one or more counter-ion(s) selected from the group of $Mg^{2+}$, $Ca^{2+}$, $Sr^{2+}$, $Ba^{2+}$.

Another property of a polyelectrolyte is the high linear charge density (number of charged groups per unit length).

Generally neutral hydrocolloids are less soluble whereas polyelectrolytes are more soluble.

Many hydrocolloids also gel. Gels are liquid-water-containing networks showing solid-like behavior with characteristic strength, dependent on their concentration, and hardness and brittleness dependent on the structure of the hydrocolloid(s) present.

Hydrogels are hydrophilic crosslinked polymers that are capable of swelling to absorb and hold vast amounts of water. They are particularly known from their use in sanitary products. Commonly used materials make use of polyacrylates, but hydrogels may be made by crosslinking soluble hydrocolloids to make an insoluble but elastic and hydrophilic polymer.

Examples of hydrocolloids comprise: Agar agar, Alginate, Arabinoxylan, Carrageenan, Carboxymethylcellulose, Cellulose, Curdlan, Gelatine, Gellan, β-Glucan, Guar gum, Gum arabic, Locust bean gum, Pectin, Starch, Xanthan gum.

In one embodiment, the at least one hydrocolloid is selected from the group consisting of gelatine, pectin, starch, alginate, agar agar, carrageenan, gellan gum, guar gum, gum arabic, locust bean gum, xanthan gum, cellulose derivatives such as carboxymethylcellulose, arabinoxylan, cellulose, curdlan, β-glucan.

Examples of polyelectrolytic hydrocolloids comprise: gelatine, pectin, alginate, carrageenan, gum arabic, xanthan gum, cellulose derivatives such as carboxymethylcellulose.

In one embodiment, the at least one hydrocolloid is a polyelectrolytic hydrocolloid.

In one embodiment, the at least one hydrocolloid is selected from the group consisting of gelatine, pectin, alginate, carrageenan, gum arabic, xanthan gum, cellulose derivatives such as carboxymethylcellulose.

In one embodiment, the at least one hydrocolloid is a gel former.

In one embodiment, the at least one hydrocolloid is used in form of a salt, such as a salt of Na+, K+, NH4+, Mg2+, Ca2+, Sr2+, Ba2+.

Gelatine

Gelatine is derived from chemical degradation of collagen. Gelatine is water soluble and has a molecular weight of 10,000 to 500,000 g/mol, such as 30,000 to 300,000 g/mol dependent on the grade of hydrolysis. Gelatine is a widely used food product and it is therefore generally accepted that this compound is totally non-toxic and therefore no precautions are to be taken when handling gelatine.

Gelatine is a heterogeneous mixture of single or multi-stranded polypeptides, typically showing helix structures. Specifically, the triple helix of type I collagen extracted from skin and bones, as a source for gelatine, is composed of two α1(I) and one α2(I) chains.

Gelatine solutions may undergo coil-helix transitions.

A-type gelatins are produced by acidic treatment. B-type gelatines are produced by basic treatment.

Chemical cross-links may be introduced to gelatine. In one embodiment, transglutaminase is used to link lysine to glutamine residues; in one embodiment, glutaraldehyde is used to link lysine to lysine, in one embodiment, tannins are used to link lysine residues.

The gelatine can also be further hydrolyzed to smaller fragments of down to 3000 g/mol.

On cooling a gelatine solution, collagen like helices may be formed.

Other hydrocolloids may also comprise helix structures such as collagen like helices. Gelatine may form helix structures.

In one embodiment, the cured binder comprising hydrocolloid comprises helix structures.

In one embodiment, the at least one hydrocolloid is a low strength gelatine, such as a gelatine having a gel strength of 30 to 125 Bloom.

In one embodiment, the at least one hydrocolloid is a medium strength gelatine, such as a gelatine having a gel strength of 125 to 180 Bloom.

In one embodiment, the at least one hydrocolloid is a high strength gelatine, such as a gelatine having a gel strength of 180 to 300 Bloom.

In a preferred embodiment, the gelatine is preferably originating from one or more sources from the group consisting of mammal, bird species, such as from cow, pig, horse, fowl, and/or from scales, skin of fish.

In one embodiment, urea may be added to the binder compositions according to the present invention. The inventors have found that the addition of even small amounts of urea causes denaturation of the gelatine, which can slow down the gelling, which might be desired in some embodiments. The addition of urea might also lead to a softening of the product.

The inventors have found that the carboxylic acid groups in gelatines interact strongly with trivalent and tetravalent ions, for example aluminium salts. This is especially true for type B gelatines which contain more carboxylic acid groups than type A gelatines.

The present inventors have found that in some embodiments, curing/drying of binder compositions according to the present invention including gelatin should not start off at very high temperatures.

The inventors have found that starting the curing at low temperatures may lead to stronger products. Without being bound to any particular theory, it is assumed by the inventors that starting curing at high temperatures may lead to an impenetrable outer shell of the binder composition which hinders water from underneath to get out.

Surprisingly, the binders according to the present invention including gelatines are very heat resistant. The present inventors have found that in some embodiments the cured binders can sustain temperatures up to 300° C. without degradation.

Pectin

Pectin is a heterogeneous grouping of acidic structural polysaccharides, found in fruit and vegetables which form acid-stable gels.

Generally, pectins do not possess exact structures, instead it may contain up to 17 different monosaccharides and over 20 types of different linkages. D-galacturonic acid residues form most of the molecules.

Gel strength increases with increasing Ca2+ concentration but reduces with temperature and acidity increase (pH<3).

Pectin may form helix structures.

The gelling ability of the di-cations is similar to that found with alginates (Mg2+ is much less than for Ca2+, Sr2+ being less than for Ba2+).

Alginate

Alginates are scaffolding polysaccharides produced by brown seaweeds.

Alginates are linear unbranched polymers containing β-(1,4)-linked D-mannuronic acid (M) and α-(1,4)-linked L-guluronic acid (G) residues. Alginate may also be a bacterial alginate, such as which are additionally O-acetylated. Alginates are not random copolymers but, according to the source algae, consist of blocks of similar and strictly alternating residues (that is, MMMMMM, GGGGGG and GMGMGMGM), each of which have different conformational preferences and behavior. Alginates may be prepared with a wide range of average molecular weights (50-100000 residues). The free carboxylic acids have a water molecule H3O+ firmly hydrogen bound to carboxylate. Ca2+ ions can replace this hydrogen bonding, zipping guluronate, but not mannuronate, chains together stoichiometrically in a so-called egg-box like conformation. Recombinant epimerases with different specificities may be used to produce designer alginates.

Alginate may form helix structures.

Carrageenan

Carrageenan is a collective term for scaffolding polysaccharides prepared by alkaline extraction (and modification) from red seaweed.

Carrageenans are linear polymers of about 25,000 galactose derivatives with regular but imprecise structures, dependent on the source and extraction conditions. κ-carrageenan (kappa-carrageenan) is produced by alkaline elimination from μ-carrageenan isolated mostly from the tropical seaweed *Kappaphycus alvarezii* (also known as *Eucheuma cottonii*).

ι-carrageenan (iota-carrageenan) is produced by alkaline elimination from ν-carrageenan isolated mostly from the Philippines seaweed *Eucheuma denticulatum* (also called Spinosum).

λ-carrageenan (lambda-carrageenan) (isolated mainly from *Gigartina pistillata* or *Chondrus crispus*) is converted into θ-carrageenan (theta-carrageenan) by alkaline elimination, but at a much slower rate than causes the production of ι-carrageenan and κ-carrageenan.

The strongest gels of κ-carrageenan are formed with K+ rather than Li+, Na+, Mg2+, Ca2+, or Sr2+.

All carrageenans may form helix structures.

Gum Arabic

Gum arabic is a complex and variable mixture of arabinogalactan oligosaccharides, polysaccharides and glycoproteins. Gum arabic consists of a mixture of lower relative molecular mass polysaccharide and higher molecular weight hydroxyproline-rich glycoprotein with a wide variability.

Gum arabic has a simultaneous presence of hydrophilic carbohydrate and hydrophobic protein.

Xanthan Gum

Xanthan gum is a microbial desiccation-resistant polymer prepared e.g. by aerobic submerged fermentation from Xanthomonas campestris.

Xanthan gum is an anionic polyelectrolyte with a β-(1,4)-D-glucopyranose glucan (as cellulose) backbone with side chains of -(3,1)-α-linked D-mannopyranose-(2,1)-β-D-glucuronic acid-(4,1)-β-D-mannopyranose on alternating residues.

Xanthan gums natural state has been proposed to be bimolecular antiparallel double helices. A conversion between the ordered double helical conformation and the single more-flexible extended chain may take place at between 40° C.-80° C.

Xanthan gums may form helix structures.

Xanthan gums may contain cellulose.

Cellulose Derivatives

An example of a cellulose derivative is carboxymethylcellulose.

Carboxymethylcellulose (CMC) is a chemically modified derivative of cellulose formed by its reaction with alkali and chloroacetic acid.

The CMC structure is based on the β-(1,4)-D-glucopyranose polymer of cellulose. Different preparations may have different degrees of substitution, but it is generally in the range 0.6-0.95 derivatives per monomer unit.

Agar Agar

Agar agar is a scaffolding polysaccharide prepared from the same family of red seaweeds (Rhodophycae) as the carrageenans. It is commercially obtained from species of *Gelidium* and *Gracilariae*.

Agar agar consists of a mixture of agarose and agaropectin. Agarose is a linear polymer, of relative molecular mass (molecular weight) about 120,000, based on the -(1,3)-β-D-galactopyranose-(1,4)-3,6-anhydro-α-L-galactopyranose unit.

Agaropectin is a heterogeneous mixture of smaller molecules that occur in lesser amounts.

Agar agar may form helix structures.

Arabinoxylan

Arabinoxylans are naturally found in the bran of grasses (Graminiae).

Arabinoxylans consist of α-L-arabinofuranose residues attached as branch-points to β-(1,4)-linked D-xylopyranose polymeric backbone chains.

Arabinoxylan may form helix structures.

Cellulose

Cellulose is a scaffolding polysaccharide found in plants as microfibrils (2-20 nm diameter and 100-40 000 nm long). Cellulose is mostly prepared from wood pulp. Cellulose is also produced in a highly hydrated form by some bacteria (for example, *Acetobacter xylinum*).

Cellulose is a linear polymer of β-(1,4)-D-glucopyranose units in 4C1 conformation. There are four crystalline forms, Iα, Iβ, II and III.

Cellulose derivatives may be methyl cellulose, hydroxypropyl methylcellulose, hydroxyethyl methylcellulose, hydroxyethyl cellulose, hydroxypropyl cellulose.

Curdlan

Curdlan is a polymer prepared commercially from a mutant strain of *Alcaligenes faecalis* var. myxogenes. Curdlan (curdlan gum) is a moderate relative molecular mass, unbranched linear 1,3 β-D glucan with no side-chains.

Curdlan may form helix structures.

Curdlan gum is insoluble in cold water but aqueous suspensions plasticize and briefly dissolve before producing reversible gels on heating to around 55° C. Heating at higher temperatures produces more resilient irreversible gels, which then remain on cooling.

Scleroglucan is also a 1,3 β-D glucan but has additional 1,6 β-links that confer solubility under ambient conditions.

Gellan

Gellan gum is a linear tetrasaccharide 4)-L-rhamnopyranosyl-(α-1,3)-D-glucopyranosyl-(β-1,4)-D-glucuronopyranosyl-(β-1,4)-D-glucopyranosyl-(β-1, with O(2) L-glyceryl and O(6) acetyl substituents on the 3-linked glucose.

Gellan may form helix structures.

β-Glucan

β-Glucans occur in the bran of grasses (Gramineae).

β-Glucans consist of linear unbranched polysaccharides of linked β-(1,3)- and β-(1,4)-D-glucopyranose units in a non-repeating but non-random order.

Guar Gum

Guar gum (also called guaran) is a reserve polysaccharide (seed flour) extracted from the seed of the leguminous shrub *Cyamopsis tetragonoloba*.

Guar gum is a galactomannana similar to locust bean gum consisting of a (1,4)-linked β-D-mannopyranose backbone with branch points from their 6-positions linked to α-D-galactose (that is, 1,6-linked-α-D-galactopyranose).

Guar gum is made up of non-ionic polydisperse rod-shaped polymer.

Unlike locust bean gum, it does not form gels.

Locust Bean Gum

Locust bean gum (also called Carob bean gum and Carubin) is a reserve polysaccharide (seed flour) extracted from the seed (kernels) of the carob tree (*Ceratonia siliqua*).

Locust bean gum is a galactomannana similar to guar gum consisting of a (1,4)-linked β-D-mannopyranose backbone with branch points from their 6-positions linked to α-D-galactose (that is, 1,6-linked α-D-galactopyranose).

Locust bean gum is polydisperse consisting of non-ionic molecules.

Starch

Starch consists of two types of molecules, amylose (normally 20-30%) and amylopectin (normally 70-80%). Both consist of polymers of α-D-glucose units in the 4C1 conformation. In amylose these are linked -(1,4)-, with the ring oxygen atoms all on the same side, whereas in amylopectin about one residue in every twenty or so is also linked -(1,6)- forming branch-points. The relative proportions of amylose to amylopectin and -(1,6)- branch-points both depend on the source of the starch. The starch may derive from the source of corn (maize), wheat, potato, tapioca and rice. Amylopectin (without amylose) can be isolated from 'waxy' maize starch whereas amylose (without amylopectin) is best isolated after specifically hydrolyzing the amylopectin with pullulanase.

Amylose may form helix structures.

In one embodiment, the at least one hydrocolloid is a functional derivative of starch such as cross-linked, oxidized, acetylated, hydroxypropylated and partially hydrolyzed starch.

In a preferred embodiment, the binder composition comprises at least two hydrocolloids, wherein one hydrocolloid is gelatine and the at least one other hydrocolloid is selected from the group consisting of pectin, starch, alginate, agar agar, carrageenan, gellan gum, guar gum, gum arabic, locust bean gum, xanthan gum, cellulose derivatives such as carboxymethylcellulose, arabinoxylan, cellulose, curdlan, β-glucan.

In one embodiment, the binder composition comprises at least two hydrocolloids, wherein one hydrocolloid is gelatine and the at least other hydrocolloid is pectin.

In one embodiment, the binder composition comprises at least two hydrocolloids, wherein one hydrocolloid is gelatine and the at least one other hydrocolloid is alginate.

In one embodiment, the binder composition comprises at least two hydrocolloids, wherein one hydrocolloid is gelatine and the at least one other hydrocolloid is carboxymethylcellulose.

In a preferred embodiment, the binder composition according to the present invention comprises at least two hydrocolloids, wherein one hydrocolloid is gelatine and wherein the gelatine is present in the binder composition in an amount of 10 to 95 wt.-%, such as 20 to 80 wt.-%, such as 30 to 70 wt.-%, such as 40 to 60 wt.-%, based on the weight of the hydrocolloids.

In one embodiment, the binder composition comprises at least two hydrocolloids, wherein the one hydrocolloid and the at least one other hydrocolloid have complementary charges.

In one embodiment, the one hydrocolloid is one or more of gelatine or gum arabic having complementary charges from one or more hydrocolloid(s) selected from the group of pectin, alginate, carrageenan, xanthan gum or carboxymethylcellulose.

In one embodiment, the binder composition is capable of curing at a temperature of not more than 95° C., such as 5-95° C., such as 10-80° C., such as 20-60° C., such as 40-50° C.

In one embodiment, the binder composition according to the present invention is not a thermoset binder.

A thermosetting composition is in a soft solid or viscous liquid state, preferably comprising a prepolymer, preferably comprising a resin, that changes irreversibly into an infusible, insoluble polymer network by curing. Curing is typically induced by the action of heat, whereby typically temperatures above 95° C. are needed.

A cured thermosetting resin is called a thermoset or a thermosetting plastic/polymer—when used as the bulk material in a polymer composite, they are referred to as the thermoset polymer matrix. In one embodiment, the aqueous binder composition according to the present invention does not contain a poly(meth)acrylic acid, a salt of a poly(meth)acrylic acid or an ester of a poly(meth)acrylic acid.

In one embodiment, the at least one hydrocolloid is a biopolymer or modified biopolymer.

Biopolymers are polymers produced by living organisms. Biopolymers may contain monomeric units that are covalently bonded to form larger structures.

There are three main classes of biopolymers, classified according to the monomeric units used and the structure of the biopolymer formed: Polynucleotides (RNA and DNA), which are long polymers composed of 13 or more nucleotide monomers; Polypeptides, such as proteins, which are polymers of amino acids; Polysaccharides, such as linearly bonded polymeric carbohydrate structures.

Polysaccharides may be linear or branched; they are typically joined with glycosidic bonds. In addition, many saccharide units can undergo various chemical modifications, and may form parts of other molecules, such as glycoproteins.

In one embodiment, the at least one hydrocolloid is a biopolymer or modified biopolymer with a polydispersity index regarding molecular mass distribution of 1, such as 0.9 to 1.

In one embodiment, the binder composition comprises proteins from animal sources, including collagen, gelatine, and hydrolysed gelatine, and the binder composition further comprises at least one phenol and/or quinone containing compound, such as tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the binder composition comprises proteins from animal sources, including collagen, gelatine, and hydrolysed gelatine, and wherein the binder composition further comprises at least one enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the binder composition is formaldehyde-free.

In one embodiment, the binder composition according to the present invention is consisting essentially of:
at least one hydrocolloid;
optionally at least one oil;
optionally at least one pH-adjuster;
optionally at least one crosslinker;
optionally at least one anti-fouling agent;
optionally at least one anti-swelling agent;
water.

In one embodiment, the at least one oil is a non-emulsified hydrocarbon oil.

In one embodiment, the at least one oil is an emulsified hydrocarbon oil.

In one embodiment, the at least one oil is a plant-based oil.

In one embodiment, the at least one crosslinker is tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the at least one crosslinker is an enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the at least one anti-swelling agent is tannic acid and/or tannins.

In one embodiment, the at least one anti-fouling agent is an antimicrobial agent.

Antimicrobial agents may be benzoic acid, propionic acid, sodium benzoate, sorbic acid, and potassium sorbate to inhibit the outgrowth of both bacterial and fungal cells.

However, natural biopreservatives may be used. Chitosan is regarded as being antifungal and antibacterial. The most frequently used biopreservatives for antimicrobial are lysozyme and nisin. Common other biopreservatives that may be used are bacteriocins, such as lacticin and pediocin and antimicrobial enzymes, such as chitinase and glucose oxidase. Also, the use of the enzyme lactoperoxidase (LPS) presents antifungal and antiviral activities. Natural antimicrobial agents may also be used, such as tannins, rosemary, and garlic essential oils, oregano, lemon grass, or cinnamon oil at different concentrations.

In one embodiment, the at least one hydrocolloid is present in the binder composition in an amount of 1 to 50, such as 2.5 to 25 wt.-%, based on the weight of the binder composition.

In one embodiment, the gelatine is present in the aqueous binder composition in an amount of 10 to 95 wt.-%, such as 20 to 80 wt.-%, such as 30 to 70 wt.-%, such as 40 to 60 wt.-%, based on the weight of the hydrocolloids.

In the method of providing thermal and/or acoustic insulation according to the present invention, the binder composition is blended with the substrate before, during or after application of the substrate to the structure.

When the binder composition is blended with the substrate before application of the substrate to the structure, the step of blending preferably occurs not more than 20 minutes before application of the mixture (the mixture being the substrate and binder composition blended together) to the structure, more preferably not more than 10 minutes, most preferably not more than 5 minutes. This minimizes curing of the binder composition prior to application of the mixture to the structure to be insulated.

When the binder composition is blended with the substrate during application to the structure, preferably the binder composition and substrate are applied simultaneously to the structure.

In a preferred embodiment, the substrate and binder composition are applied to the structure by spraying, blowing or pouring.

Most preferably, the binder composition and substrate are applied simultaneously by spraying. This can be, for instance, by means of blending the substrate and binder composition to form a mixture and then spraying the mixture through one or more nozzles. Alternatively the substrate(s) and binder composition may be sprayed from separate nozzles to form a single blended stream, which is applied to the structure. As a further option the two or more streams may be blended at the point of application to the structure.

When the substrate comprises two or more components then these may be blended prior to blending with the binder composition, or applied separately but simultaneously, as for the substrate and binder composition options given above.

In embodiments where the binder composition comprises two or more components they are usually blended prior to further blending with the substrate. However, it is possible for them to be applied separately, as for the substrate and binder composition options given above When the binder composition is blended with the substrate after application of the substrate to the structure, preferably the step of blending occurs not more than 20 minutes after application of the substrate to the structure, more preferably not more than 10 minutes, most preferably not more than 5 minutes. This minimizes curing of the binder before the substrate and binder have been fully blended.

In appropriate cases, the substrate and binder composition are applied to at least one surface of the structure, for example, at least one wall. Alternatively, the substrate and binder composition may be applied to a cavity or space in a structure, such as a cavity wall.

In the method of the present invention, the binder composition is allowed to cure after application of the substrate and binder composition to the structure. Preferably, the binder composition is allowed to cure at ambient temperature, that is, at the temperature existing at the site of the structure, without application of a heat source. Ambient temperature may be from 10° C. to 40° C. In another preferred embodiment, curing of the binder application preferably occurs at temperatures from 5° C. to 95° C., such as 5 to 80° C., such as 8 to 50° C. more preferably 10° C. to 40° C. If it is desired to cure at a temperature different from the ambient temperature the structure or its surroundings may be heated or cooled Preferably the step of curing occurs in the order of minutes or hours.

The curing is defined as a process whereby the binder composition undergoes a physical and/or chemical reaction which in case of a chemical reaction usually increases the molecular weight of the compounds in the binder composition and thereby increases the viscosity of the binder composition, usually until the binder composition reaches a solid state.

In one embodiment the curing process comprises cross-linking and/or water inclusion as crystal water.

In one embodiment the cured binder contains crystal water that may decrease in content and raise in content depending on the prevailing conditions of temperature, pressure and humidity.

In one embodiment the curing process comprises drying by pressure. The pressure may be applied by blowing air or gas over/through the mixture of fibres and optionally particulate material and binder. The blowing process may be accompanied by heating or cooling or it may be at ambient temperature.

In one embodiment, the curing process comprises drying by blowing air or gas over/through the substrate or by increasing the temperature.

In one embodiment the curing process takes place in a humid environment. The humid environment may have a relative humidity RH of 60-99%, such as 70-95%, such as 80-92%. The curing in a humid environment may be followed by curing or drying to obtain a state of the prevalent humidity.

Once the binder composition is cured, the substrate and binder composition mixture appears coherent.

The blend of substrate and cured binder composition preferably has a density of from 10 to 900 kg/m3.

For use as an acoustic regulation material (e.g. sound absorption), the blend of substrate and cured binder composition may have a density of from 60 to 200 kg/m3, preferably from 80 to 150 kg/m3.

Sound absorption may be defined as a material with a weighted sound absorption coefficient $\alpha_w \geq 0.8$ (Absorption class A and B—EN ISO 11654).

For use as a thermal insulation material, the blend of substrate and cured binder composition may have a density of from 10 to 200 kg/m3, preferably from 30 to 100 kg/m3.

Thermal insulation may be defined as a material with a lambda value at 10° C. of $\lambda \leq 0.060$ W/m K.

The present invention also relates to an insulated structure obtainable by the above described method. In particular, a second aspect of the invention is an insulated structure obtainable by:

providing a substrate which comprises fibres;
applying the substrate to the structure;
blending the substrate with a binder composition before, during or after application of the substrate to the structure;
allowing curing of the binder composition after the substrate and the binder composition have been applied to the structure;
wherein the binder composition comprises at least one hydrocolloid.

The insulated structure may be any structure but is preferably a wall, a cavity wall, a ceiling, a floor, an attic or a roof of a building or a building component. The insulated structure preferably provides thermal and/or acoustic insulation.

In this aspect of the invention any of the features discussed above with respect to the first aspect may be applied.

The insulated product made according to the present invention comprises a binder resulting from the curing of a binder composition comprising a hydrocolloid, as described in the first aspect of the invention.

In one embodiment, the loss on ignition (LOI) of the mass of substrate bonded by the binder according to the present invention is within the range of 0.1 to 25.0%, such as 0.3 to 18.0%, such as 0.5 to 12.0%, such as 0.7 to 8.0% by weight.

The insulated product may have a weight % binder solids in the substrate of from 0.1 to 50.0%, such as 0.3 to 36.0%, such as 0.5 to 24.0%, such as 0.7 to 16.0%, such as 1.4 to 12.0%, such as 2.0 to 8.0%, based on the weight of the substrate.

In one embodiment, the binder is not crosslinked.
In an alternative embodiment, the binder is crosslinked.

Reaction of the Binder Components

The present inventors have found that in some embodiments the insulated products made according to the present invention are best to be produced when the binder is applied to the substrate under acidic conditions. Therefore, in a preferred embodiment, the binder applied to the substrate comprises a pH-adjuster, in particular in form of a pH buffer.

In a preferred embodiment, the binder in its uncured state has a pH value of less than 8, such as less than 7, such as less than 6.

The present inventors have found that in some embodiments, the curing of the binder is strongly accelerated under alkaline conditions. Therefore, in one embodiment, the binder composition comprises a pH-adjuster, preferably in form of a base, such as organic base, such as amine or salts thereof, inorganic bases, such as metal hydroxide, such as KOH or NaOH, ammonia or salts thereof.

In a particular preferred embodiment, the pH adjuster is an alkaline metal hydroxide, in particular NaOH.

In a preferred embodiment, the binder composition according to the present invention has a pH of 7 to 10, such as 7.5 to 9.5, such as 8 to 9.

Other additives may be components such as one or more reactive or nonreactive silicones and may be added to the binder. Preferably, the one or more reactive or nonreactive silicone is selected from the group consisting of silicone constituted of a main chain composed of organosiloxane residues, especially diphenylsiloxane residues, alkylsiloxane residues, preferably dimethylsiloxane residues, bearing at least one hydroxyl, acyl, carboxyl or anhydride, amine, epoxy or vinyl functional group capable of reacting with at least one of the constituents of the binder composition and is preferably present in an amount of 0.1-15 weight-%, preferably from 0.1-10 weight-%, more preferably 0.3-8 weight-%, based on the total binder mass.

In one embodiment, an oil may be added to the binder composition.

In one embodiment, the at least one oil is a non-emulsified hydrocarbon oil.

In one embodiment, the at least one oil is an emulsified hydrocarbon oil.

In one embodiment, the at least one oil is a plant-based oil.

In one embodiment, the at least one crosslinker is tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the at least one crosslinker is an enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the at least one anti-swelling agent is tannic acid and/or tannins.

In one embodiment, the at least one anti-fouling agent is an antimicrobial agent. Antimicrobial agents may be benzoic acid, propionic acid, sodium benzoate, sorbic acid, and potassium sorbate to inhibit the outgrowth of both bacterial and fungal cells. However, natural biopreservatives may be used. Chitosan is regarded as being antifungal and antibacterial. The most frequently used biopreservatives for antimicrobial are lysozyme and nisin. Common other biopreservatives that may be used are bacteriocins, such as lacticin and pediocin and antimicrobial enzymes, such as chitinase and glucose oxidase. Also, the use of the enzyme lactoperoxidase (LPS) presents antifungal and antiviral activities. Natural antimicrobial agents may also be used, such as tannins, rosemary, and garlic essential oils, oregano, lemon grass, or cinnamon oil at different concentrations.

In one embodiment, an anti-fouling agent may be added to the binder.

In a preferred embodiment, the anti-fouling agent is a tannin, in particular a tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, an anti-swelling agent may be added to the binder, such as tannic acid and/or tannins.

Further additives may be additives containing calcium ions and antioxidants.

In one embodiment, the binder composition according to the present invention contains additives in form of linkers containing acyl groups and/or amine groups and/or thiol groups. These linkers can strengthen and/or modify the network of the cured binder.

In one embodiment, the binder compositions according to the present invention contain further additives in form of additives selected from the group consisting of PEG-type reagents, silanes, and hydroxylapatites.

EXAMPLES

In the following examples, several binders which fall under the definition of the present invention were prepared and compared to binders according to the prior art.

Binders According to the Prior Art

The following properties were determined for the binders according the prior art.

Reagents

Silane (Momentive VS-142) was supplied by Momentive and was calculated as 100% for simplicity. All other components were supplied in high purity by Sigma-Aldrich and were assumed anhydrous for simplicity unless stated otherwise.

Binder Component Solids Content—Definition

The content of each of the components in a given binder solution before curing is based on the anhydrous mass of the components. The following formula can be used:

$$\text{Binder component solids content (\%)} = \frac{\text{binder component } A \text{ solids } (g) + \text{binder component } B \text{ solids } (g) + \ldots}{\text{total weight of mixture } (g)} \times 100\%$$

Binder Solids—Definition and Procedure

The content of binder after curing is termed "binder solids".

Disc-shaped stone wool samples (diameter: 5 cm; height 1 cm) were cut out of stone wool and heat-treated at 580° C. for at least 30 minutes to remove all organics. The solids of the binder mixture (see below for mixing examples) were measured by distributing a sample of the binder mixture (approx. 2 g) onto a heat treated stone wool disc in a tin foil container. The weight of the tin foil container containing the stone wool disc was weighed before and directly after addition of the binder mixture. Two such binder mixture loaded stone wool discs in tin foil containers were produced and they were then heated at 200° C. for 1 hour. After cooling and storing at room temperature for 10 minutes, the samples were weighed and the binder solids were calculated as an average of the two results. A binder with the desired binder solids could then be produced by diluting with the required amount of water and 10% aq. silane (Momentive VS-142).

Reaction Loss—Definition

The reaction loss is defined as the difference between the binder component solids content and the binder solids.

Mechanical Strength Studies (Bar Tests)—Procedure

The mechanical strength of the binders was tested in a bar test. For each binder, 16 bars were manufactured from a mixture of the binder and stone wool shots from the stone wool spinning production. The shots are particles which have the same melt composition as the stone wool fibers, and the shots are normally considered a waste product from the spinning process. The shots used for the bar composition have a size of 0.25-0.50 mm.

A 15% binder solids binder solution containing 0.5% silane (Momentive VS-142) of binder solids was obtained as described above under "binder solids". A sample of this binder solution (16.0 g) was mixed well with shots (80.0 g). The resulting mixture was then divided evenly into four slots in a heat resistant silicone form for making small bars (4×5 slots per form; slot top dimension: length=5.6 cm, width=2.5 cm; slot bottom dimension: length=5.3 cm, width=2.2 cm; slot height=1.1 cm). The mixtures placed in the slots were then pressed hard with a suitably sized flat metal bar to generate even bar surfaces. 16 bars from each binder were made in this fashion. The resulting bars were then cured at 200° C. for 1 h. After cooling to room temperature, the bars were carefully taken out of the containers. Eight of the 16 bars were aged in an autoclave (15 min/120° C./1.2 bar).

After drying for 1-2 days, all bars were then broken in a 3 point bending test (test speed: 10.0 mm/min; rupture level: 50%; nominal strength: 30 N/mm$^2$; support distance: 40 mm; max deflection 20 mm; nominal e-module 10000 N/mm$^2$) on a Bent Tram machine to investigate their mechanical strengths. The bars were placed with the "top face" up (i.e. the face with the dimensions length=5.6 cm, width=2.5 cm) in the machine.

Loss of Ignition (LOI) of Bars

The loss of ignition (LOI) of bars was measured in small tin foil containers by treatment at 580° C. For each measurement, a tin foil container was first heat-treated at 580° C. for 15 minutes to remove all organics. The tin foil container was allowed to cool to ambient temperature, and was then weighed. Four bars (usually after being broken in the 3 point bending test) were placed into the tin foil container and the ensemble was weighed. The tin foil container containing bars was then heat-treated at 580° C. for 30 minutes, allowed to cool to ambient temperature, and finally weighed again. The LOI was then calculated using the following formula:

$$LOI\ (\%) = \frac{\text{Weight of bars before heat treatment } (g) - \text{Weight of bars after heat treatment } (g)}{\text{Weight of bars before heat treatment } (g)} \times 100\%$$

Reference Binders from the Prior Art Prepared as Comparative Examples

Binder Example, Reference Binder A (Phenol-Formaldehyde Resin Modified with Urea, a PUF-Resol)

A phenol-formaldehyde resin is prepared by reacting 37% aq. formaldehyde (606 g) and phenol (189 g) in the presence of 46% aq. potassium hydroxide (25.5 g) at a reaction temperature of 84° C. preceded by a heating rate of approximately 1° C. per minute. The reaction is continued at 84° C. until the acid tolerance of the resin is 4 and most of the phenol is converted. Urea (241 g) is then added and the mixture is cooled. The acid tolerance (AT) expresses the number of times a given volume of a binder can be diluted with acid without the mixture becoming cloudy (the binder precipitates). Sulfuric acid is used to determine the stop criterion in a binder production and an acid tolerance lower than 4 indicates the end of the binder reaction. To measure the AT, a titrant is produced from diluting 2.5 mL conc. sulfuric acid (>99%) with 1 L ion exchanged water. 5 mL of the binder to be investigated is then titrated at room temperature with this titrant while keeping the binder in motion by manually shaking it; if preferred, use a magnetic stirrer and a magnetic stick. Titration is continued until a slight cloud appears in the binder, which does not disappear when the binder is shaken.

The acid tolerance (AT) is calculated by dividing the amount of acid used for the titration (mL) with the amount of sample (mL):

AT=(Used titration volume (mL))/(Sample volume (mL))

Using the urea-modified phenol-formaldehyde resin obtained, a binder is made by addition of 25% aq. ammonia (90 mL) and ammonium sulfate (13.2 g) followed by water (1.30 kg). The binder solids were then measured as described above and the mixture was diluted with the required amount of water and silane (Momentive VS-142)

for mechanical strength studies (15% binder solids solution, 0.5% silane of binder solids).

Binders According to the Present Invention

The following properties were determined for the binders according the present invention.

Reagents

Gelatines (Speisegelatine, type A, porcine, 120 and 180 bloom; ImageI LB, type B, 122 bloom) were obtained from Gelita AG. Tannorouge chestnut tree tannin was obtained from Brouwland bvba. Agar agar (05039), gellan gum (P8169), pectin from citrus peel (P9135), sodium alginate from brown algae (A0682), sodium carboxymethyl cellulose (419303), soluble starch (S9765), and sodium hydroxide were obtained from Sigma-Aldrich. For simplicity, these reagents were considered completely pure and anhydrous.

Binder Component Solids Content—Definition

The content of each of the components in a given binder solution before curing is based on the anhydrous mass of the components. The following formula can be used:

$$\text{Binder component solids content } (\%) = \frac{\text{binder component } A \text{ solids } (g) + \text{binder component } B \text{ solids } (g) + \ldots}{\text{total weight of mixture } (g)} \times 100\%$$

Mechanical Strength Studies (Bar Tests)—Procedure

The mechanical strength of the binders was tested in a bar test. For each binder, 8-16 bars were manufactured from a mixture of the binder and stone wool shots from the stone wool spinning production. The shots are particles which have the same melt composition as the stone wool fibers, and the shots are normally considered a waste product from the spinning process. The shots used for the bar composition have a size of 0.25-0.50 mm.

A binder solution was obtained as described in the examples below. For comparatively slower setting binders, a sample of the binder solution (16.0 g for binders with 10-15% binder component solids; 32.0 g for binders with 5% binder component solids) was mixed well with shots (80.0 g). The resulting mixture was then divided evenly into four slots in a heat resistant silicone form for making small bars (4×5 slots per form; slot top dimension: length=5.6 cm, width=2.5 cm; slot bottom dimension: length=5.3 cm, width=2.2 cm; slot height=1.1 cm). For comparatively faster setting binders, a sample of the binder solution (8.0 g for binders with 10-15% binder component solids and 16.0 g for binders with 5% binder component solids) was mixed well with shots (40.0 g, pre-heated to 35-40° C. before use), and the resulting mixture was then divided evenly into two slots only. During the manufacture of each bar, the mixtures placed in the slots were pressed as required and then evened out with a plastic spatula to generate an even bar surface. 8-16 bars from each binder were made in this fashion. The resulting bars were then cured at room temperature for 1-2 days or first cured for 15 minutes in an oven at the temperatures listed in the tables followed by curing for 1-2 days at room temperature. If still not sufficiently cured after that time, the bars were cured for 1 day at 35° C. The bars were then carefully taken out of the containers, turned upside down and left for a day at room temperature to cure completely. Half of the 8-16 bars were aged in an autoclave (15 min/120° C./1.2 bar).

After drying for 1-2 days, all bars were then broken in a 3 point bending test (test speed: 10.0 mm/min; rupture level: 50%; nominal strength: 30 N/mm$^2$; support distance: 40 mm; max deflection 20 mm; nominal e-module 10000 N/mm$^2$) on a Bent Tram machine to investigate their mechanical strengths. The bars were placed with the "top face" up (i.e. the face with the dimensions length=5.6 cm, width=2.5 cm) in the machine.

Loss of Ignition (LOI) of Bars

The loss of ignition (LOI) of bars was measured in small tin foil containers by treatment at 580° C. For each measurement, a tin foil container was first heat-treated at 580° C. for 15 minutes to remove all organics. The tin foil container was allowed to cool to ambient temperature, and was then weighed. Four bars (usually after being broken in the 3 point bending test) were placed into the tin foil container and the ensemble was weighed. The tin foil container containing bars was then heat-treated at 580° C. for 30 minutes, allowed to cool to ambient temperature, and finally weighed again. The LOI was then calculated using the following formula:

$$LOI \ (\%) = \frac{\text{Weight of bars before heat treatment } (g) - \text{Weight of bars after heat treatment } (g)}{\text{Weight of bars before heat treatment } (g)} \times 100\%$$

Binder Example, Entry 1

A mixture of gelatine (Speisegelatine, type A, porcine, 120 bloom, 7.5 g) in water (42.5 g) was stirred at 50° C. for approx. 15-30 min until a clear solution was obtained (pH 5.1). The resulting solution was then used in the subsequent experiments.

Binder Example, Entry 3

A mixture of gelatine (Speisegelatine, type A, porcine, 180 bloom, 8.82 g) in water (50.0 g) was stirred at 50° C. for approx. 15-30 min until a clear solution was obtained (pH 5.2). The resulting solution was then used in the subsequent experiments.

Binder Example, Entry 5

A mixture of gelatine (ImageI LB, type B, 122 bloom, 8.82 g) in water (50.0 g) was stirred at 50° C. for approx. 15-30 min until a clear solution was obtained (pH 5.1). The resulting solution was then used in the subsequent experiments.

Binder Example, Entry 7

To water (50.0 g) stirred vigorously at 85° C. was added sodium carboxymethyl cellulose (2.63 g) portion-wise over approx. 15 minutes. Stirring was continued for 0.5-1 h further at 85° C. until a clear solution was obtained (pH 8.4). The resulting solution was then used in the subsequent experiments.

Binder Example, Entry 8

To water (50.0 g) stirred vigorously at 85° C. was added soluble starch (2.63 g) portion-wise over approx. 15 minutes. Stirring was continued for 0.5-1 h further at 85° C. until a clear solution was obtained (pH 6.4). The resulting solution was then used in the subsequent experiments.

Binder Example, Entry 9

To water (50.0 g) stirred vigorously at 85° C. was added agar agar (2.63 g) portion-wise over approx. 15 minutes. Stirring was continued for 0.5-1 h further at 85° C. until a clear solution was obtained.

A mixture of gelatine (Speisegelatine, type A, porcine, 120 bloom, 8.82 g) in water (50.0 g) was stirred at 50° C. for approx. 15-30 min until a clear solution was obtained. A portion of the above agar agar solution (19.6 g, thus efficiently 0.98 g agar agar and 18.6 g water) was then added and stirring was continued at 50° C. for 5 min further (pH 5.3). The resulting solution was then used in the subsequent experiments.

Binder Example, Entry 10

To water (50.0 g) stirred vigorously at 85° C. was added gellan gum (2.63 g) portion-wise over approx. 15 minutes. Stirring was continued for 0.5-1 h further at 85° C. until a clear solution was obtained.

A mixture of gelatine (Speisegelatine, type A, porcine, 120 bloom, 8.82 g) in water (50.0 g) was stirred at 50° C. for approx. 15-30 min until a clear solution was obtained. A portion of the above gellan gum solution (19.6 g, thus efficiently 0.98 g gellan gum and 18.6 g water) was then added and stirring was continued at 50° C. for 5 min further (pH 5.3). The resulting solution was then used in the subsequent experiments.

Binder Example, Entry 11

To water (50.0 g) stirred vigorously at 85° C. was added pectin (2.63 g) portion-wise over approx. 15 minutes. Stirring was continued for 0.5-1 h further at 85° C. until a clear solution was obtained.

A mixture of gelatine (Speisegelatine, type A, porcine, 120 bloom, 8.82 g) in water (50.0 g) was stirred at 50° C. for approx. 15-30 min until a clear solution was obtained. A portion of the above pectin solution (19.6 g, thus efficiently 0.98 g pectin and 18.6 g water) was then added and stirring was continued at 50° C. for 5 min further (pH 4.8). The resulting solution was then used in the subsequent experiments.

Binder Example, Entry 12

To water (50.0 g) stirred vigorously at 85° C. was added sodium alginate (2.63 g) portion-wise over approx. 15 minutes. Stirring was continued for 0.5-1 h further at 85° C. until a clear solution was obtained.

A mixture of gelatine (Speisegelatine, type A, porcine, 120 bloom, 8.82 g) in water (50.0 g) was stirred at 50° C. for approx. 15-30 min until a clear solution was obtained. A portion of the above sodium alginate solution (19.6 g, thus efficiently 0.98 g sodium alginate and 18.6 g water) was then added and stirring was continued at 50° C. for 5 min further (pH 5.3). The resulting solution was then used in the subsequent experiments.

Binder Example, Entry 13

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 8.00 g) in water (72.0 g) was stirred at 50° C. for approx. 15-30 min until a clear solution was obtained (pH 4.8). 1M NaOH (3.50 g) was then added (pH 9.3) followed by a portion of the above chestnut tree tannin solution (3.60 g; thus efficiently 0.80 g chestnut tree tannin). After stirring for 1-2 minutes further at 50° C., the resulting brown mixture (pH 9.2) was used in the subsequent experiments.

Binder Example, Entry 14

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.9). 1M NaOH (4.00 g) was then added (pH 9.1) followed by a portion of the above chestnut tree tannin solution (4.50 g; thus efficiently 1.00 g chestnut tree tannin). After stirring for 1-2 minutes further at 50° C., the resulting brown mixture (pH 9.1) was used in the subsequent experiments.

Binder Example, Entry 17

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 180 bloom, 10.0 g) in water (56.7 g) was stirred at 50° C. for approx. 15-30 min until a clear solution was obtained (pH 4.8). 1M NaOH (3.50 g) was then added (pH 9.2) followed by a portion of the above chestnut tree tannin solution (4.50 g; thus efficiently 1.00 g chestnut tree tannin). After stirring for 1-2 minutes further at 50° C., the resulting brown mixture (pH 9.2) was used in the subsequent experiments.

Binder Example, Entry 19

To 1M NaOH (15.75 g) stirred at room temperature was added chestnut tree tannin (4.50 g). Stirring was continued at room temperature for 5-10 min further, yielding a deep red-brown solution.

A mixture of gelatine (ImageI LB, type B, 122 bloom, 10.0 g) in water (56.7 g) was stirred at 50° C. for approx. 15-30 min until a clear solution was obtained (pH 4.7). 1M NaOH (3.50 g) was then added (pH 9.2) followed by a portion of the above chestnut tree tannin solution (4.50 g; thus efficiently 1.00 g chestnut tree tannin). After stirring for 1-2 minutes further at 50° C., the resulting brown mixture (pH 9.2) was used in the subsequent experiments.

Binder Example, Entry 21

To water (50.0 g) stirred vigorously at 85° C. was added agar agar (2.63 g) portion-wise over approx. 15 minutes. Stirring was continued for 0.5-1 h further at 85° C. until a clear solution was obtained.

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.6). 1M NaOH (4.00 g) was then added (pH 9.1) followed by a portion of the above chestnut tree tannin solution (4.50 g; thus efficiently 1.00 g chestnut tree tannin) and then a portion of the above agar agar solution (20.0 g; thus efficiently 1.00 g agar agar). After stirring for 1-2 minutes further at 50° C., the resulting brown mixture (pH 8.8) was used in the subsequent experiments.

Binder Example, Entry 22

To water (50.0 g) stirred vigorously at 85° C. was added pectin (2.63 g) portion-wise over approx. 15 minutes. Stirring was continued for 0.5-1 h further at 85° C. until a clear solution was obtained.

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.6). 1M NaOH (4.50 g) was then added (pH 9.6) followed by a portion of the above chestnut tree tannin solution (4.50 g; thus efficiently 1.00 g chestnut tree tannin) and then a portion of the above pectin solution (20.0 g; thus efficiently 1.00 g pectin). After stirring for 1-2 minutes further at 50° C., the resulting brown mixture (pH 8.9) was used in the subsequent experiments.

Binder Example, Entry 23

To water (50.0 g) stirred vigorously at 85° C. was added sodium alginate (2.63 g) portion-wise over approx. 15 minutes. Stirring was continued for 0.5-1 h further at 85° C. until a clear solution was obtained.

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.6). 1M NaOH (4.00 g) was then added (pH 9.2) followed by a portion of the above chestnut tree tannin solution (4.50 g; thus efficiently 1.00 g chestnut tree tannin) and then a portion of the above sodium alginate solution (20.0 g; thus efficiently 1.00 g sodium alginate). After stirring for 1-2 minutes further at 50° C., the resulting brown mixture (pH 9.0) was used in the subsequent experiments.

Binder Example, Entry 24

To water (50.0 g) stirred vigorously at 85° C. was added soluble starch (2.63 g) portion-wise over approx. 15 minutes. Stirring was continued for 0.5-1 h further at 85° C. until a clear solution was obtained.

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.8). 1M NaOH (4.00 g) was then added (pH 9.1) followed by a portion of the above chestnut tree tannin solution (4.50 g; thus efficiently 1.00 g chestnut tree tannin) and then a portion of the above soluble starch solution (20.0 g; thus efficiently 1.00 g soluble starch). After stirring for 1-2 minutes further at 50° C., the resulting brown mixture (pH 8.8) was used in the subsequent experiments.

TABLE 1-1

| Reference binder | |
|---|---|
| Example | A |
| Binder properties | |
| Binder solids (%) | 15.0 |
| Reaction loss (%) | 28.5 |
| pH | 9.6 |
| Bar curing conditions | |
| Temperature (° C./1 h) | 200 |
| Bar properties | |
| Mechanical strength, unaged (kN) | 0.39 |
| Mechanical strength, aged (kN) | 0.28 |
| LOI, unaged (%) | 2.8 |

TABLE 1-2

| Various hydrocolloids | | | | | | | | | | | | |
|---|---|---|---|---|---|---|---|---|---|---|---|---|
| Example | 1 | 2 | 3 | 4 | 5 | 6 | 7 | 8 | 9 | 10 | 11 | 12 |
| Binder composition | | | | | | | | | | | | |
| Hydrocolloid (%-wt.) | | | | | | | | | | | | |
| Gelatine, Speisegelatine, 120 bloom | 100 | 100 | — | — | — | — | — | — | 90 | 90 | 90 | 90 |
| Gelatine, Speisegelatine, 180 bloom | — | — | 100 | 100 | — | — | — | — | — | — | — | — |
| Gelatine, Imagel LB, 122 bloom | — | — | — | — | 100 | 100 | — | — | — | — | — | — |
| Agar agar | — | — | — | — | — | — | — | — | 10 | — | — | — |
| Gellan gum | — | — | — | — | — | — | — | — | — | 10 | — | — |
| Pectin | — | — | — | — | — | — | — | — | — | — | 10 | — |
| Sodium alginate | — | — | — | — | — | — | — | — | — | — | — | 10 |
| Sodium carboxymethyl cellulose | — | — | — | — | — | — | 100 | — | — | — | — | — |
| Soluble starch | — | — | — | — | — | — | — | 100 | — | — | — | — |
| Crosslinker (%-wt.) [a] | | | | | | | | | | | | |
| Chestnut tree tannin | | | | | | | | | | | | |
| Base (%-wt.) [b] | | | | | | | | | | | | |
| Sodium hydroxide | | | | | | | | | | | | |
| Binder mixing and bar manufacture | | | | | | | | | | | | |
| Mixing temperature (° C.) | 50 | 50 | 50 | 50 | 50 | 50 | 85 | 85 | 50/85 | 50/85 | 50/85 | 50/85 |
| Binder component solids content (%) | 15.0 | 10.0 | 15.0 | 10.0 | 15.0 | 10.0 | 5.0 | 5.0 | 12.5 | 12.5 | 12.5 | 12.5 |
| pH | 5.1 | 4.9 | 5.2 | 4.9 | 5.1 | 5.0 | 8.4 | 6.4 | 5.3 | 5.3 | 4.8 | 5.3 |
| Pre-heated shots (35-40° C.) | — | — | Yes | Yes | — | — | — | — | — | — | — | — |
| Curing Temperature (° C./15 min to rt) | rt | rt | rt | rt | rt | rt | rt | rt | rt | rt | rt | rt |
| Bar properties | | | | | | | | | | | | |
| Mechanical strength, unaged (kN) | 0.31 | 0.24 | 0.28 | 0.13 | 0.20 | 0.13 | 0.13 | 0.11 | 0.11 | 0.09 | 0.13 | 0.13 |

TABLE 1-2-continued

| Various hydrocolloids | | | | | | | | | | | | |
|---|---|---|---|---|---|---|---|---|---|---|---|---|
| Example | 1 | 2 | 3 | 4 | 5 | 6 | 7 | 8 | 9 | 10 | 11 | 12 |
| Mechanical strength, aged (kN) | 0.30 | 0.28 | 0.27 | 0.17 | 0.22 | 0.15 | 0.15 | 0.12 | 0.15 | 0.11 | 0.14 | 0.22 |
| LOI, unaged (%) | 2.9 | 1.9 | 2.9 | 1.9 | 2.8 | 1.9 | 1.9 | 2.0 | 2.4 | 2.5 | 2.4 | 2.3 |

[a] Of hydrocolloid(s).
[b] Of hydrocolloid(s) + crosslinker.

TABLE 1-3

| Various hydrocolloids, crosslinkers | | | | | | | | | | | | |
|---|---|---|---|---|---|---|---|---|---|---|---|---|
| Example | 13 | 14 | 15 | 16 | 17 | 18 | 19 | 20 | 21 | 22 | 23 | 24 |
| Binder composition | | | | | | | | | | | | |
| Polyelectrolytic hydrocolloid (%-wt.) | | | | | | | | | | | | |
| Gelatine, Speisegelatine, 120 bloom | 100 | 100 | 100 | 100 | — | — | — | — | 91 | 91 | 91 | 91 |
| Gelatine, Speisegelatine, 180 bloom | — | — | — | — | 100 | 100 | — | — | — | — | — | — |
| Gelatine, Imagel LB, 122 bloom | — | — | — | — | — | — | 100 | 100 | — | — | — | — |
| Agar agar | — | — | — | — | — | — | — | — | 9 | — | — | — |
| Gellan gum | — | — | — | — | — | — | — | — | — | — | — | — |
| Pectin | — | — | — | — | — | — | — | — | — | 9 | — | — |
| Sodium alginate | — | — | — | — | — | — | — | — | — | — | 9 | — |
| Sodium carboxymethyl cellulose | — | — | — | — | — | — | — | — | — | — | — | — |
| Soluble starch | — | — | — | — | — | — | — | — | — | — | — | 9 |
| Crosslinker (%-wt.) [a] | | | | | | | | | | | | |
| Chestnut tree tannin | 10 | 10 | 10 | 10 | 10 | 10 | 10 | 10 | 9 | 9 | 9 | 9 |
| Base (%-wt.) [b] | | | | | | | | | | | | |
| Sodium hydroxide | 2.7 | 2.6 | 2.6 | 2.6 | 2.4 | 2.4 | 2.4 | 2.4 | 2.4 | 2.5 | 2.4 | 2.4 |
| Binder mixing and bar manufacture | | | | | | | | | | | | |
| Mixing temperature (° C.) | 50 | 50 | 50 | 50 | 50 | 50 | 50 | 50 | 50/85 | 50/85 | 50/85 | 50/85 |
| Binder component solids content (%) | 10.4 | 15.0 | 15.0 | 15.0 | 15.1 | 15.1 | 15.1 | 15.1 | 12.9 | 12.9 | 12.9 | 12.9 |
| pH | 9.2 | 9.1 | 9.1 | 9.1 | 9.2 | 9.2 | 9.2 | 9.2 | 8.8 | 8.9 | 9.0 | 8.8 |
| Pre-heated shots (35-40° C.) | — | — | — | — | Yes | Yes | — | — | — | — | — | — |
| Curing Temperature (° C./15 min to rt) | rt | rt | 35 | 55 | 35 | 55 | 35 | 55 | rt | rt | rt | rt |
| Bar properties | | | | | | | | | | | | |
| Mechanical strength, unaged (kN) | 0.16 | 0.23 | 0.26 | 0.27 | 0.30 | 0.27 | 0.25 | 0.27 | 0.16 | 0.18 | 0.17 | 0.18 |
| Mechanical strength, aged (kN) | 0.15 | 0.21 | 0.25 | 0.25 | 0.25 | 0.31 | 0.27 | 0.26 | 0.15 | 0.13 | 0.15 | 0.18 |
| LOI, unaged (%) | 1.9 | 2.7 | 2.7 | 2.7 | 2.7 | 2.8 | 2.8 | 2.8 | 2.4 | 2.6 | 2.4 | 2.4 |

[a] Of hydrocolloid(s).
[b] Of hydrocolloid(s) + crosslinker

As can be seen from comparing the results in Table 1.1 with Tables 1.2 and 1.3, the binder compositions used in the present invention require lower temperatures for curing. The reference binder composition requires temperatures of 200° C. for curing, while binder compositions 1 to 24 cure at 55° C. and below, typically at ambient temperature. This means that the binder compositions of the present invention are capable of being cured on-site, rather than at the manufacturing or process stage.

The invention claimed is:
1. A method of providing thermal and/or acoustic insulation to a structure, comprising the steps of:
   providing a substrate which comprises fibres;
   applying the substrate to the structure;
   blending the substrate with a binder composition before, during or after application of the substrate to the structure;
   allowing curing of the binder composition after the substrate and the binder composition have been applied to the structure;
   wherein the binder composition comprises at least one hydrocolloid, wherein the at least one hydrocolloid is a protein from animal sources; and
   wherein the binder composition comprises:
      at least one phenol containing compound; and/or
      at least one enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), catechol oxi- dase, tyrosine oxidase, and phenoloxidase, lysyl oxidase (EC 1.4.3.13), and peroxidase (EC 1.11.1.7).

2. The method according to claim 1, wherein the substrate does not comprise mineral wool.

3. The method according to claim 1, wherein the substrate comprises fibres which are mineral fibres.

4. The method according to claim 1, wherein the substrate also comprises a particulate material.

5. The method according to claim 4, wherein the substrate comprises particulate material selected from the group consisting of aerogel, perlite, vermiculite, xonolite, phase-change material, micro-spheres and fire retardant.

6. The method according to claim 1, wherein the fibres do not comprise any binder composition before the substrate is blended with the binder composition.

7. The method according to claim 1, wherein the fibres are in the form of a granulate of flocks of fibres bonded with a cured binder composition.

8. The method according to claim 1, wherein the structure is any one of a wall, a cavity wall, a ceiling, a floor, an attic, or a roof of a building or a building component.

9. The method according to claim 1 wherein the step of blending the substrate with the binder composition occurs during application of the substrate to the structure, by simultaneously applying the substrate and the binder composition to the structure.

10. The method according to claim 9, wherein the substrate and the binder composition are applied simultaneously by spraying.

11. The method according to claim 1, wherein curing of the binder composition occurs at temperatures from 5 to 95° C.

12. The method according to claim 11, wherein curing of the binder composition occurs at temperatures from 8 to 50° C.

13. The method according to claim 12, wherein curing of the binder composition occurs at temperatures from 10 to 40° C.

14. The method according to claim 1, wherein the step of blending the substrate with the binder composition occurs not more than 20 minutes before application of the substrate to the structure.

15. The method according to claim 14, wherein the step of blending the substrate with the binder composition occurs not more than 5 minutes before application of the substrate to the structure.

16. The method according to claim 1, wherein the binder composition comprises at least two hydrocolloids, wherein one hydrocolloid is gelatine and the at least one other hydrocolloid is selected from the group consisting of pectin, starch, alginate, agar agar, carrageenan, gellan gum, guar gum, gum arabic, locust bean gum, xanthan gum, and cellulose derivatives.

17. The method according to claim 16, wherein the cellulose derivatives are selected from the group consisting of carboxymethylcellulose, arabinoxylan, cellulose, curdlan, and 6-glucan.

18. The method according to claim 16, wherein the gelatine is present in the binder composition in an amount of 10 to 95 wt.-% based on the weight of the hydrocolloids.

19. The method according to claim 18, wherein the gelatine is present in the binder composition in an amount of 40 to 60 wt.-%, based on the weight of the hydrocolloids.

20. The method according to claim 1, wherein the binder composition is not a thermoset binder.

21. The method according to claim 1, wherein the binder composition does not contain a poly(meth)acrylic acid, a salt of a poly(meth)acrylic acid or an ester of a poly(meth)acrylic acid.

22. The method according to claim 1, wherein the binder composition comprises at least one phenol containing compound, which is a tannin selected from one or more components from the group consisting of tannic acid, condensed tannins (proanthocyanidins), hydrolysable tannins, gallotannins, ellagitannins, complex tannins, and tannin originating from one or more of oak, chestnut, staghorn sumac and fringe cups.

23. The method according to claim 22, wherein the at least one hydrocolloid of the binder composition is gelatine.

24. The method according to claim 1, wherein the at least one hydrocolloid of the binder composition is gelatine, and wherein the binder composition comprises at least one enzyme which is transglutaminase (EC 2.3.2.13).

25. The method according to claim 1, wherein the binder composition is formaldehyde-free.

26. The method according to claim 1, wherein the method does not involve crosslinking of the binder composition.

27. The method according to claim 1, wherein the method does involve crosslinking of the binder composition.

28. The method according to claim 1, wherein the curing process comprises a drying process by blowing air or gas over/through the substrate or by increasing temperature.

29. An insulated structure obtained by the method according to claim 1.

30. The method according to claim 1, wherein the at least one protein from animal sources comprises at least one of collagen, gelatine and hydrolysed gelatine.

31. An insulated structure according to claim 29, which is any one of a wall, a cavity wall, a ceiling, a floor, an attic, or a roof of a building or a building component.

32. The insulated structure according to claim 29, wherein the loss on ignition (LOI) of the mass of substrate bonded by binder is within the range of 0.1 to 25.0% by weight.

33. The insulated structure according to claim 32, wherein the loss on ignition (LOI) of the mass of substrate bonded by binder is within the range of 0.5 to 12.0% by weight.

34. The insulated structure according to claim 33, wherein the loss on ignition (LOI) of the mass of substrate bonded by binder is within the range of 0.7 to 8.0% by weight.

* * * * *

UNITED STATES PATENT AND TRADEMARK OFFICE
CERTIFICATE OF CORRECTION

| | | |
|---|---|---|
| PATENT NO. | : 11,919,283 B2 | Page 1 of 1 |
| APPLICATION NO. | : 16/300608 | |
| DATED | : March 5, 2024 | |
| INVENTOR(S) | : Hjelmgaard et al. | |

It is certified that error appears in the above-identified patent and that said Letters Patent is hereby corrected as shown below:

On the Title Page

Item (73) Assignee reads: "ROCKWOOL A/S, Hedehusense(DK)"
Should read --ROCKWOOL A/S, Hedehusene (DK)--

Signed and Sealed this
Fifth Day of August, 2025

Coke Morgan Stewart
*Acting Director of the United States Patent and Trademark Office*